United States Patent [19]

Charatan

[11] Patent Number: 5,174,314
[45] Date of Patent: Dec. 29, 1992

[54] ORAL HYGIENE DEVICE

[76] Inventor: Norman Charatan, 22 Varady Dr., Fords, N.J. 08863

[21] Appl. No.: 716,064

[22] Filed: Jun. 17, 1991

[51] Int. Cl.[5] ............................................. A61C 15/00
[52] U.S. Cl. .................................... 132/328; 132/321
[58] Field of Search ................ 132/321, 323, 324, 328, 132/329, 325, 326, 327

[56] References Cited

U.S. PATENT DOCUMENTS

| | | | |
|---|---|---|---|
| 817,050 | 4/1906 | De La Cour | 132/325 |
| 3,696,821 | 10/1972 | Adams, IV | 132/324 |
| 3,799,177 | 3/1974 | Bragg | 132/325 |
| 3,831,611 | 8/1974 | Hendricks | 132/324 |
| 4,403,625 | 9/1983 | Sanders et al. | 132/328 |
| 4,519,408 | 5/1985 | Charatan | 132/321 |
| 4,633,892 | 1/1987 | Charatan | 132/321 |
| 4,836,227 | 6/1989 | Charaton | 132/321 |
| 4,986,289 | 1/1991 | McWhorter | 132/323 |

*Primary Examiner*—Gene Mancene
*Assistant Examiner*—Frank A. LaViola
*Attorney, Agent, or Firm*—Mathews, Woodbridge & Collins

[57] ABSTRACT

An oral hygiene device employs a hollow plastic tube sealed at both ends. At least one area along the length of the tube is weakened and has its diameter in the weakened area reduced, but not reduced to zero diameter. A length of fiber, such as conventional dental floss well known as a tooth cleaning material is stored within the length of the tube comprising the housing and has each of the free ends secured to a bulk of rigid material whose size does not permit the fibrous material from being able to escape the narrow diameter area. In use, a user bends the unbroken tubing housing to a point that the tubing breaks into at least two pieces, allowing the fibrous flossing material to be positioned intermediate the separated portions of the tubing, which are now free to act as handles. After its use, the fibrous material and the two handles may be discarded. In its use the fibrous material is kept clean until it is used and virtually an unlimited force may be placed on the handles and the fibrous material in its cleaning use without separation or breakage.

11 Claims, 2 Drawing Sheets

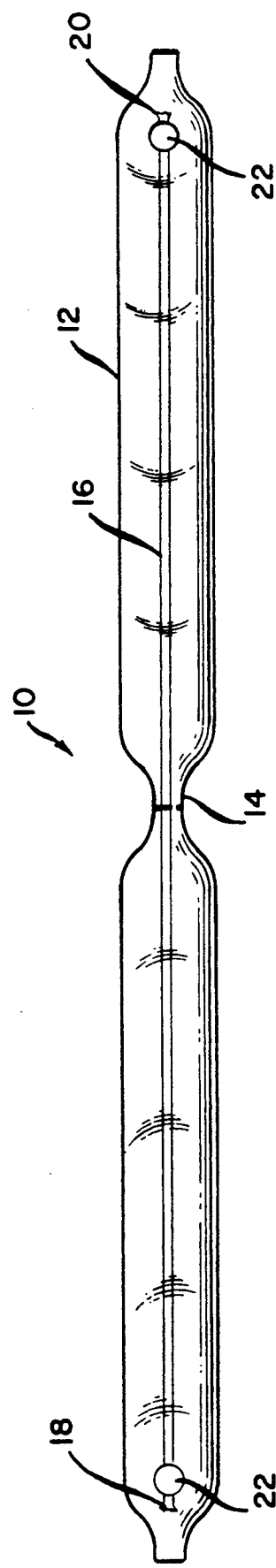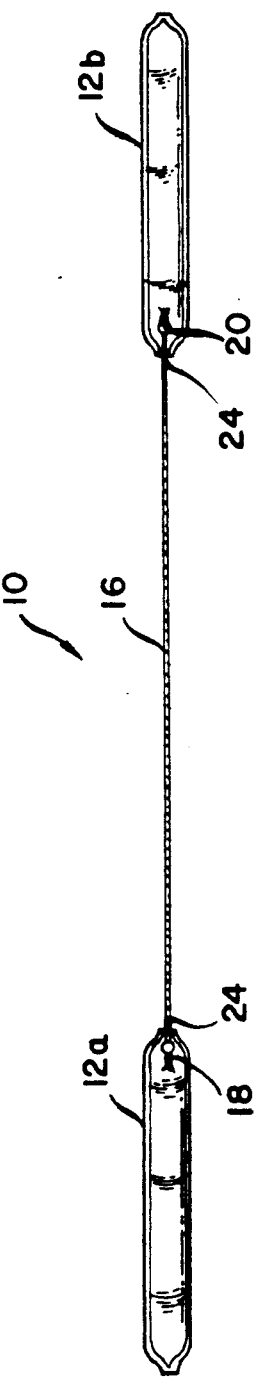

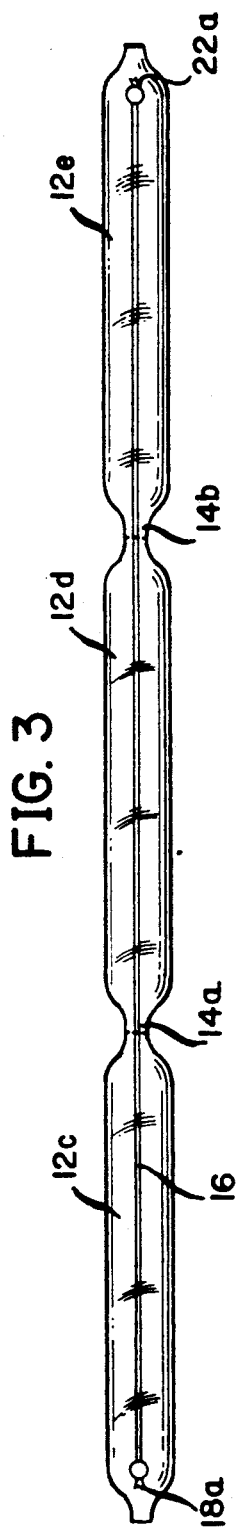
FIG. 3
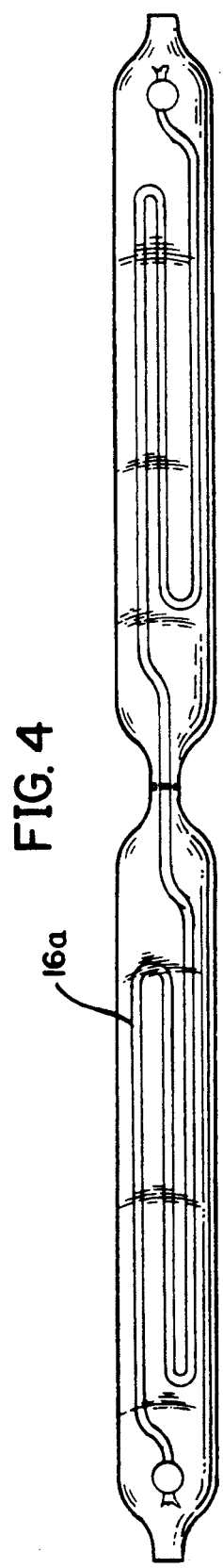
FIG. 4
FIG. 5
FIG. 6

ORAL HYGIENE DEVICE

BACKGROUND OF THE INVENTION

1. The Field of the Invention

This invention concerns dental flossing devices having handles for ease of use.

2. Description of the Prior Art

The prior art abounds with various types of flossing devices. Amongst these are rolls of dental floss, a portion of the length thereof being available for separation from the roll and used by the user wrapping a portion near each end around a finger and allowing the central region to be used in the tooth cleaning operation. Some forms of devices have the free ends of the floss or fibrous material sealed to a housing, which when separated may act as handles. However, in order to obtain a length of floss for the cleaning use, it must be packed within the housing, being a costly and difficult thing to do. I have previously invented an apparatus which consists of a housing containing a plastic type material, which when placed under tension, after separating the housing, expands its length to form an elongated flossing material. However, the strength of the extended material is not as great as the conventional fibrous flossing material used in other devices.

SUMMARY OF THE INVENTION

The present invention overcomes the problems and limitations of the prior art and succeeds in accomplishing the objects hereinabove set forth by providing a device which may be fabricated in an in-line method continuously, by securing to conventional dental floss material one or more rigid bulks of a plastic material whose diameter is slightly larger than the one or more reduced diameters between the ends of the housing. Thus, when the housing is separated into two or more sections, the ends of the floss material are kept within the housing adjacent the area of its ends, permitting its bulk of its length to emerge from the handles for use. If there are two weakened areas, a first free portion of the floss is used in a cleaning operation. Afterwards, the second weakened portion permits another length of the floss material to be used. If desired, the floss material can be folded when stored within the housing, or, if stored along the length of the housing without folding, virtually the entire length of the floss is available as a cleaning device. If the floss is captured in a housing of the same length and the housing has only one weakened area, then the length of floss available for cleaning is limited to the length of the housing in a single cleaning operation. If the housing has more than one weakened area, the length of floss stored within the housing may have a minimal length equal to the housing length or a greater length as desired. In such case, only portions of the total length of floss are available dependent on the separating of different portions of the housing, those portions adjacent the exposed portions acting as handles.

Accordingly, the present invention has as an object a device which stores a conventional floss material in a housing until ready for use by breaking the housing into at least two portions.

Another object is a housing which provides two handles when the housing is separated into two or more portions.

Still another object is to provide a cleaning device whose flossing element is not fixed to the housing and is provided with bulk ends that prevent the flossing material from being freed from the housing.

These objects, as well as other objects of the present invention, will become still more readily apparent after reading the following description of the accompanying drawings.

BRIEF DESCRIPTION OF THE DRAWINGS

FIG. 1 is a plan view of an embodiment of the present invention.

FIG. 2 is a plan view of the apparatus as shown in FIG. 1 when separated into two sections.

FIG. 3 is a plan view of another embodiment of the present invention.

FIG. 4 is still another embodiment of the present invention.

FIG. 5 is a plan view of a portion of the present invention shown in FIG. 1, showing the formation of an end thereof.

FIG. 6 is a plan view of a portion of the embodiment shown in FIG. 1 illustrating another formation of an end thereof.

DESCRIPTION OF THE PREFERRED EMBODIMENT

The structure and method of fabrication of the present invention is applicable to a dental flossing device consisting of an elongated cylindrical housing. The housing has at least one central portion thereof having a reduced diameter. A conventional flossing material is stored whithin the housing. The otherwise free ends of the flossing material are secured to plastic bulk elements whose diameters are larger than the reduced diameter of the housing in its central region. When the reduced diameter of the housing is used to break the housing into at least two sections, the floss material has its otherwise free ends restrained from total release from the housing ends, but permitting the bulk of the length of the floss from extending from the two ends of the housing for use in a cleaning operation where the floss is captured within the housing only near the free ends of the floss. Before the housing is separated into at least two portions all of the floss is kept totally clean by the housing. After the separation of the housing, the separated parts may act as handles, avoiding the need for the user to wrap the floss about the fingers of the user.

In another embodiment the housing may contain two or more weakened areas thus permitting two or more separate parts of the floss to be used in separate cleaning operations.

In still another embodiment of the present invention the stored floss material may be folded up so that a greater length of floss than the total length of the housing may be available for use, and the floss length will not be limited to the total length of the housing, if desired.

The ends of the housing may be finished with a tapered end or with a pointed end so as to permit the handles to be used in a manner similar to a tooth pick. This is in addition to the flossing capability made possible by the floss material.

Now referring to the figures, and more particularly to the embodiment illustrated in FIG. 1 showing the present invention 10 having a housing 12. The central region has a reduced internal diameter 14 that is less than the diameter of the balance of the housing. Stored within the housing is a length of dental floss 16. A rigid bulk of plastic material 22 is secured to the ends 18 and 20 of floss 16. The rigid plastic bulk material 22 has a larger diameter than the internal diameter 14 of the central region of the housing 12. Thus, the floss can never completely escape the housing by the size of the plastic bulk material acting as a stop. However the balance of the floss length is free to escape the housing and be used in a standard cleaning operation with handles.

FIG. 2 illustrates the housing when separated into two lengths 12a and 12b. Floss length 16 is permitted to be exposed from the housing after the separation of the housing into two portions 12a and 12b. Bulk portions of plastic 18 and 20 prevent the ends of the floss from escaping the housing ends completely because openings 14 are less than the size of the plastic bulk at each end of the floss but large enough to permit the balance of the length of the floss to freely exit the interior of the housing.

FIG. 3 shows the housing having two reduced internal diameter areas 14a and 14b along the length of the housing, dividing the housing into sections 12c and 12d and 12e. When the housing is separated at area 14a, floss material 16 is permitted to escape section 12c and 12d by a length of floss 16 consisting of a length of floss 16 from end 18a to 14a as well as length of floss 16 from end 20a to narrow section 14b. Thus effectively the entire length of the floss is made available for a cleaning operation except for the contained length of the floss 16 captured by the length of housing length 12d. Later, after the separation of housing lengths 12d and 12e another section of the floss is free to emerge from the housing exposing a clean length for use by shifting section 12d towards section 12c. After the use of all of the floss sections the entire device is discarded.

FIG. 4 shows housing 12 containing an elongated length of floss 16a obtained by folding up the length of floss and storing same within the housing having the free ends thereof secured to bulks of plastic which prevents the floss ends from totally escaping from the housing when the housing is separated.

FIG. 5 illustrates an end of the housing having a tapered form 26 obtained by forming the housing, using heat and pressure. In this shaped end a tooth pick like function may be obtained.

FIG. 6 illustrates a pointed end 28 on one side of the housing used as a tooth pick which may be used as a tooth cleaning operation.

In practice I have found that the reduced internal diameter can have a diameter of 0.010 inches for a housing having an internal diameter of about 0.035 inches. The plastic bulk stop material can be fabricated from E. I. Duponts "Bynel" and applied as a hot melt to form a blob having a cold diameter of 0.025 inches. Thus the blob can move freely within the housing but cannot pass the reduced diameter of about 0.010 inches, thus capturing the ends of the floss within the housing. The "Bynel" being an ethylene terpolymer material which readily adheres to the floss. A hotmelt comprising nylon may also be used to form the bulk ends. The floss material is well known in the trade and may have scents and other medicaments added to the floss. The floss may consist of a Nylon base multi-filament having an 840 denier of the type 715 as made by E. I. Dupont. If desired the floss may be coated with wax and also be coated with fluorides.

Thus, there is disclosed in the above description and in the drawings, an embodiment of the invention which fully and effectively accomplishes the objects thereof. However, it will become apparent to those skilled in the art, how to make variations and modifications to the instant invention. Therefore, this invention is limited, not by the specific disclosure herein, but only by the appending claims.

The embodiment of the invention in which an exclusive privilege or property is claimed are defined as follows.

I claim:

1. A tooth cleaning device comprising:
    a housing having at least one section including a first hollow interior cavity of a predetermined diameter and a first orifice with a predetermined diameter less than said diameter of said first interior cavity, said first orifice communicating with said first interior cavity;
    a length of floss material extending through said first orifice and having at least a first and a second, movable free end, said first, movable free end located inside said first interior cavity;
    a first stop means connected to said first, movable free end and having a diameter larger than the diameter of said first orifice;
    a second section of said housing having a second hollow interior cavity therein of a predetermined diameter and a second orifice with a predetermined diameter less than said diameter of said second hollow interior cavity, said second orifice communicating with said second interior cavity; and,
    a second stop means connected to said second, movable free end and having a diameter larger than the diameter of said second orifice, said second stop means and said second, movable free end located within said second hollow interior cavity,
    wherein said first stop means prevents said floss material from being completely withdrawn from said first interior cavity through said first orifice and said second stop means prevents said floss material from being completely withdrawn from said second interior cavity through said second orifice.

2. The tooth cleaning device of claim 1, wherein said first and second stop means comprise a plastic bulk of material adhered to said floss material at said first and second movable, free ends thereof.

3. The tooth cleaning device of claim 2 wherein said floss material comprises a substantially non-extendable material.

4. The tooth cleaning device of claim 3 wherein said floss material comprises a Nylon ® material.

5. The tooth cleaning device of claim 4 wherein said floss material comprises a multi-filament plastic material.

6. The tooth cleaning device of claim 5 wherein said plastic bulk of material adhered to said floss material at said first and second movable, free ends thereof comprises a hotmelt plastic material.

7. The tooth cleaning device of claim 6 wherein said housing has pointed ends at the extremes thereof, and,
    wherein the pointed ends of said housing can be used as a toothpick.

8. The tooth cleaning device of claim 7 wherein the area in the vicinity of said first and second orifices is weakened, and,
    wherein said housing can be broken at said weakened area in order to separate said first and second sections and extend said floss material therebetween.

9. The tooth cleaning device of claim 8 wherein the total extended length of said floss material is greater than the total overall length of said housing.

10. A tooth cleaning device comprising:
    a housing comprising at least a first and a second section each having a hollow interior of a predetermined diameter, said first and second sections communicating with each other through a hollow central section having a predetermined diameter less than the diameter of the interior cavities of said first and second sections;
    a continuous length of floss material located in said interior cavities of said first and second sections, said length of floss material having a first free, movable end located in the interior cavity of said first section, and a second free, movable end located in the interior cavity of said second section; and,
    stop means attached to said first and second free, movable ends of said floss material, said stop means having a diameter larger than the diameter of the central section between said first and second sections, but smaller than the diameter of the interior cavities of said first and second sections,
    wherein said stop means prevents said floss material from being completely withdrawn from the interior cavities of said first and second sections.

11. The tooth cleaning device of claim 10 wherein said stop means comprises bulk plastic material.

* * * * *